United States Patent [19]

Klaveness et al.

[11] Patent Number: 5,384,109
[45] Date of Patent: Jan. 24, 1995

[54] DIAGNOSTIC MAGNETOMETRY USING SUPERPARAMAGNETIC PARTICLES

[75] Inventors: Jo Klaveness; Thorfinn Ege, both of Oslo, Norway; Scott M. Rocklage, Los Gatos, Calif.

[73] Assignee: Nycomed Imaging AS, Oslo, Norway

[21] Appl. No.: 930,521

[22] PCT Filed: Mar. 30, 1991

[86] PCT No.: PCT/EP91/00619
§ 371 Date: Nov. 6, 1992
§ 102(e) Date: Nov. 6, 1992

[87] PCT Pub. No.: WO91/15243
PCT Pub. Date: Oct. 17, 1991

[30] Foreign Application Priority Data

Apr. 2, 1990 [GB] United Kingdom ............... 9007408

[51] Int. Cl.$^6$ ............................................. A61B 5/055
[52] U.S. Cl. ................................ 424/9; 324/653.1; 324/653.4; 436/173; 514/54; 514/60; 423/632; 423/633
[58] Field of Search ................. 424/9; 324/248; 128/653.1, 653.4, 654; 436/173; 514/54, 60; 423/632, 633; 428/549

[56] References Cited

U.S. PATENT DOCUMENTS

| | | | |
|---|---|---|---|
| 4,735,796 | 4/1988 | Gordon | 424/9 |
| 4,813,399 | 3/1989 | Gordon | 600/12 |
| 4,827,945 | 5/1989 | Groman et al. | 128/653 |
| 4,996,991 | 3/1991 | Gordon | 128/653.4 |

FOREIGN PATENT DOCUMENTS

| | | |
|---|---|---|
| WO85/02772 | 7/1985 | WIPO . |
| WO86/06605 | 11/1986 | WIPO . |
| WO88/00060 | 1/1988 | WIPO . |
| WO90/07322 | 7/1990 | WIPO . |

OTHER PUBLICATIONS

Colfield et al., *Chemical Abstracts,* 104:217805s (1986).
Day et al., *Biophys. J.,* 52, Nov. 1987, pp. 837–853.
Sundfors et al., *J. de Phys.,* Coll. C10, 46:C10.785 (1985).
Mateew, *Solid State Communications,* 31, pp. 1009–1010 (1979).
Swithenby, *Phys. Technol.,* 18, pp. 17–24 (1987).
Farrell et al., *Biomagnetism,* Walter de Gruyter, Berlin 1981, pp. 507–518.
Rassi et al., 7th Int. Conf. on Biomagnetism, New York (Aug. 1990), pp. 261–262.
Fischer et al., 7th Int. Conf. on Biomagnetism, New York (Aug. 1990), pp. 285–286.
Farrell et al., *IEEE Transactions on Magnetics,* MAG-16, 5 pp. 818–823 (1980).
Cohen, *IEEE Trasactions on Magnetics,* MAG-11, 2, pp. 694–700 (1975).

*Primary Examiner*—Gary E. Hollinden
*Attorney, Agent, or Firm*—Bacon & Thomas

[57] ABSTRACT

The use of superparamagnetic particles and of paramagnetic materials (such as lanthanide chelates) as contrast agents in magnetometric analysis, especially imaging, and in particular structural and functional, diagnosis or imaging is described.

11 Claims, 3 Drawing Sheets

DIAGNOSTIC MAGNETOMETRY USING SUPERPARAMAGNETIC PARTICLES

This invention relates to the use of paramagnetic and superparamagnetic substances as enhancing agents for diagnostic magnetometery, especially using a superconducting quantum interference device magnetometer (a SQUID) and preferably as imaging contrast agents in magnetometric imaging, in particular SQUID imaging.

In 1963 James Zimmerman, a researcher at Ford Motor Company, observed that when a non-superconducting boundary is present in a superconducting loop a special effect is created. This effect is extremely sensitive to magnetic flux and based on Zimmerman's work the very highly sensitive SQUID magnetometers have been developed and are now available commercially from companies such as Biomagnetic Technologies Inc of San Diego, Calif. and Siemens AG of West Germany.

SQUID magnetometers generally comprise a superconducting pick up coil system and a detector system (the SQUID) which itself comprises one or two Josephson junctions inserted into a loop of superconducting wire. The magnetic flux within such loops is quantized and changes in the magnetic field experienced by the pick up coils cause an immediate and measurable change in the current flowing through the detector. The SQUID magnetometers available include both single and multichannel devices, the latter being capable of detecting magnetic fields at plurality of locations simultaneously.

SQUID magnetometers are capable of measuring magnetic fields as low as $10^{-14}$ Tesla, one ten billionth the earth's magnetic field, and thus are able to detect magnetic fields generated by biological activity such as for example the fields of the order of $10^{-13}$ T which are induced by the electrical activity of the brain. The sources of nerve signals can thus be traced to within a few millimeters.

SQUIDS and their use in the study of biomagnetism are discussed for example by Wolsky et al. Scientific American, February 1989, pages 60–69, Philo et al. Rev. Sci. Instrum. 48:1529–1536 (1977), Cohen IEEE Trans. Mag. MAG-11(2):694–700 (1975), Farrell et al. Applied Physics Communications 1(1):1–7 (1981), Farrell et al. IEEE Trans. Mag. 16:818–823 (1980), and Brittenham et al. N. Eng. J. Med. 307(27):1671–1675 (1982). The SQUID may be designed to detect the magnetic field or, may be of the gradiometer type and which several designs exist.

Indeed the development of biomagnetic analysis has been closely linked to the development of SQUID detectors since conventional magnetometers, such as Bartington detectors or Hall-probe gaussmeters, are several orders of magnitude less sensitive to magnetic field changes.

In the study of biomagnetism, or more specifically, the in vive measurement of magnetic susceptibility, the sensitivity of SQUIDS has been such that the researchers' concentration has primarily been on three areas—the detection of electrical activity within body tissues by detection of the accompanying magnetic field changes, the in vive determination of iron concentrations in the liver in order to detect iron overload or iron deficiency there, and the detection of ferromagnetic particle contamination in the lungs.

In the first two cases, the magnetic fields detected by the SQUIDS arise from normal or stimulated nerve activity or from the normal presence of (paramagnetic) iron in the liver. In the third case, particle contamination is by magnetic particles, e.g. of magnetite, and their magnetic effect is first maximized by placing the subject in a magnetic field. The resultant magnetization is detectable by a SQUID for the period of months over which it decays.

Due to the extreme sensitivity of the SQUID technology enabling the body's electrical activity to be monitored, there has been little emphasis on the use of SQUIDS for the generation of images, in particular two or three dimensional images, of the body's internal physical structure rather than electrical activity images.

For such localisation to be effective it must be possible to generate magnetic susceptibility differences between different body tissues, organs and ducts and rather than doing this by provoking electrical activity or by relying on natural aggregations of non-diamagnetic material we now propose the administration in diagnostic magnetometery, especially magnetometric imaging, of enhancing agents comprising paramagnetic or superparamagnetic substances. SQUIDS are sufficiently sensitive to detect the changes in local magnetic susceptibility where such agents distribute within the body so enabling contrast enhanced magnetometric signals or images to be generated, for example for use in diagnostics.

Thus viewed from one aspect the present invention provides the use of a physiologically tolerable paramagnetic or superparamagnetic material, and in particular paramagnetic lanthanide metal ion chelates and free or matrix borne superparamagnetic particles, for the manufacture of a diagnostic agent for use in magnetometric analysis, preferably by magnetrometic imaging, of the human or non-human, preferably mammalian, animal body.

Viewed from a further aspect, the invention also provides a method of diagnosis of the human or non-human animal body which method comprises administering to said body a physiologically tolerable paramagnetic or superparamagnetic material and generating a magnetometric signal of at least a part of said body into which said material distributes, preferably but not essentially using a SQUID based system, especially a multichannel SQUID.

Viewed from another aspect the invention also provides a method of generating a magnetometric image of the human or non-human animal body which method comprises administering to said body a physiologically tolerable paramagnetic or superparamagnetic material and generating a magnetometric image of at least a part of said body into which said material distributes, in particular generating a two or three dimensional structural image and preferably but not essentially using a SQUID based imaging device, especially a multichannel SQUID imager.

Viewed from a still further aspect, the invention also provides a process for detecting variations in magnetic susceptibility within a human or non-human animal body which process comprises administering to said body a physiologically tolerable paramagnetic or superparamagnetic material, and with a magnetometer continuously or repeatedly monitoring the magnetic susceptibility of at least a part of said body into which said material distributes, for example to generate magnetometric signals or preferably images of variations or abnormalities in blood flow, or to monitor the location and aggregation of these materials within regions of the body, for example the arrival and accumulation of tissue- or organ- targeting substances at the targeted region, e.g. a tumour, the reticuloendothelial system, etc. and optionally to generate a magnetometric image thereof.

Viewed from another aspect the invention also provides the use of a physiologically tolerable paramagnetic or superparamagnetic material, and in particular paramagnetic lanthanide metal ion chelates and free or matrix borne superparamagnetic particles, for the manufacture of a diagnostic composition for use in the process according to the invention.

DETAILED DESCRIPTION OF THE INVENTION

Figure 1:
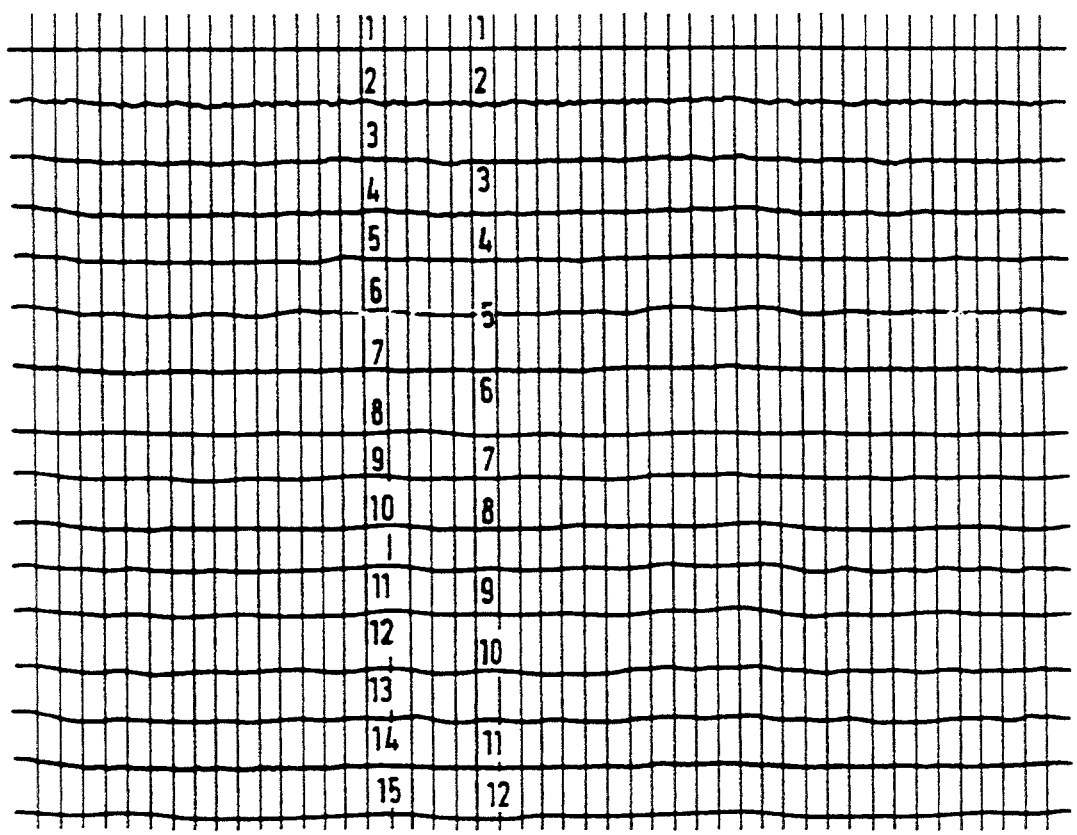
FIG. 1 represents a multichannel SQUID analysis without any sample.

The method and process of the invention may be performed using any magnetometric technique but are particularly suited to the use of SQUID based magnetometers. Thus the process of the invention for example may be performed using single channel SQUIDS but would preferably be performed using a multichannel SQUID system.

The paramagnetic or superparamagnetic substances used according to the invention and for convenience referred to herein as magnetometric diagnostic agents may, in view of the sensitivity of SQUID magnetometers, be any such material which is biotolerable in the dosages and with the administration form and route that is used. There is of course no necessity to pre-magnetize the subject following administration of the diagnostic agent before transferring the subject to the magnetometer location (generally a region of homogeneous magnetic field or a magnetically shielded room). However, the contrast agent may be pre-magnetised before administration and it may also be advantageous to pretreat the magnetic substance to prevent conglomeration thus obtaining a maximum field for a given concentration of subtance.

The process and method of the invention can be performed with or without the imposition of an external magnetic field (besides or in place of the earth's natural magnetic field that is). Imposed fields can be variant, e.g. pulsed, or invariant. Where the contrast agent used is superparamagnetic the method and particularly the process of the invention may advantageously be performed with no pre-magnetization and with no imposed magnetic field or with only a static imposed magnetic field. However where the contrast agent used is paramagnetic rather than superparamagnetic, the magnetometric investigation according to the invention will preferably be performed with the subject exposed to an imposed pulsed or invariant magnetic field, at least in the region of interest. This field can be relatively localized in effect and can be as low as $10^{-4}$ T but in one convenient embodiment may be the primary field, generally of up to $10^1$ T, generated by the primary coils of a magnetic resonance imager. Where the contrast agent is superparamagnetic an external field can be but need not be applied.

Particularly preferred diagnostic agents will include those which have relatively high magnetic susceptibilities, in particular superparamagnetic particles and substances containing high spin paramagnetic metal species, especially high spin transition metal and lanthanide ions, in particular ions of Mn, Fe, Dy, Gd, Eu, Tb, Tm, Yb, Er and Ho, most particularly Dy(III). A wide variety of such materials have been proposed for use as contrast agents in magnetic resonance imaging (MRI), and MRI contrast agents will in general also be suitable for use as magnetometric diagnostic (MD) agents, including magnetometric imaging (MI), contrast agents.

Thus particular mention may be made of the superparamagnetic contrast agents already proposed for use as MRI contrast agents by for example Jacobsen et al. in U.S. Pat. No. 4,863,716, by Klaveness et al. in WO-A-89/11873, by Schröder et al. in WO-A-85/02772, by Groman in WO-A-88/00060, by Schering in EP-A-186616, by Widder et al. in AJR 148:399–404 (1987), by Hemmingsson et al. in Acta Radiologica 28:703–705 (1987), by Hahn et al. in Society of Magnetic Resonance in Medicine, 7th Annual Meeting, 1988, Book of Abstracts, page 738, by Saini et al. in Radiology 162:211–216 (1987), by Clement et al. in CMR89. MR20 (1989), etc.

Superparamagnetic particles free and carrier-bound are widely available and their preparation is described in a large variety of references, e.g. WO-A-83/03920 (Ugelstad), WO-A-89/03675 (Schröder), WO-A-83/03426 (Schröder), WO-A-88/06632 (Josephson), U.S. Pat. No. 4,675,173, DE-A-3508000, U.S. Pat. No. 4,827,945, U.S. Pat. No. 4,951,675 and WO-A-88/00060.

The literature thus contains many suggestions for the formulation of superparamagnetic particles and in particular suggests that the particles can be administered either free (i.e. uncoated and not bound to any other substance) or coated (e.g. dextran coated—see for example U.S. Pat. No. 4,452,773) or carried by or embedded in a matrix particle (e.g. a polysaccharide—see for example WO-A-83/03920 and WO-A-85/02772) or bound to an organ or tissue targetting species, e.g. a biomolecule such as an antibody or a hormone (see for example WO-A-88/00060 and WO-A-88/06632).

Due to the sensitivity of SQUIDS, which should be able to detect very small numbers of or even single superparamagnetic crystal loaded matrix particles, tumour imaging or detection using antibody-coupled superparamagnetic particles may be of significant practical interest.

For such tumour imaging or detection, one may conveniently use superparamagnetic crystal loaded matrix particles where the matrix is coupled to an antibody, or coated, e.g. silanized, superparamagnetic crystals where the coating is coupled to an antibody, or even paramagnetic polychelates coupled to an antibody, preferably ones in which the chelated paramagnetic ions are high spin lanthanides such as Dy(III), Ho(III) and Er(III). Paramagnetic polychelates have received much attention recently as potential X-ray and MRI contrast agents and are discussed for example in WO-A-90/12050.

Parenterally administrable particulate MD agents are also of particular interest in the imaging of the liver and spleen due to the action of the reticuloendothelial system in removing such particles from the blood stream. However MD agents and especially particulate agents may also be used to advantage in the magnetometric diagnosis or imaging of body ducts and cavities having external voidance ducts, e.g. the gastrointestinal tract, the bladder and the uterus, where the MD agent can be administered orally, rectally or through a catheter into the body cavity of interest.

Many different ways of achieving tissue and organ specificity for soluble and particulate diagnostic agents are already known.

Thus by attachment to fatty acids and other substances with a specific hydrophilic/hydrophobic ratio the agent will after intravenous injection efficiently accumulate in the hepatocytes. Hepatocytes also have specific lectins present on their surface. The latter causes specific oligosaccharides and glycoproteins to accumulate in the hepatocyte compartment of the liver. The Kupffer cells as well as the endothelial cells of the liver also possess unique lectins on their surface, causing other types of glycoproteins to accumulate in these compartments. The endothelial cells of the liver have receptors for specific molecules such as hyaluronic acid, enabling other types of targeting vehicles also to be used for this compartment.

It is possible to bind the MD agent to monoclonal antibodies specific for almost any macromolecular structure. Different organs have cells containing organ-specific structures on their surface. Using monoclonal antibodies reacting with organ-specific structure, it is thus possible to produce organ-specific vehicles.

Furthermore, hormones, growth factors and lymphokines often have organ-specific receptors. Consequently, "natural" human proteins of this type may also be used as targeting vehicles.

These types of targeting vehicles will cause accumulation in normal organs, and if these are deformed and non-homogeneous due to disease, MD agents attached to such vehicles will provide important diagnostic information. However, for direct disease visualization, targeting vehicles with affinity for disease-specific structures should be employed.

Thus tumour cells possess unique surface markers, and monoclonal antibodies reacting with a number of such structures have been developed. Tumor-specific monoclonal antibodies coupled to MD agents can thus be used to obtain disease information, e.g. by visualization.

Thrombi contain a number of specific structures, for instance fibrin. Consequently, MD agents coupled to fibrin-specific antibodies will after intravenous injection accumulate in the clots, and can be used for diagnosis of the thrombi.

In the same way as Mabs with affinity for clots can be developed, the naturally occurring protein tPA has affinity for fibrin. tPA coupled MD agents would thus accumulate in thrombi and be useful for their detection.

Upon cell necrosis, intracellular structures like myocine and histones are exposed to macromolecules normally confined to the extracellular space. Coupled to MD agents Mabs against both the above structures may thus be used to visualise infarcts/necrosis.

Where superparamagnetic particle containing contrast media are administered parenterally, and especially intravascularly, the biodegradation and ultimate excretion of the particle metabolites may be enhanced by formulating the particles together with a chelating agent as described in WO-A-89/11873.

The superparamagnetic particles themselves may be of any material which, although preferably non-radioactive (unless the particles are also intended to be detected by their radioactive decay emissions), exhibits superparamagnetism in domain and sub-domain sized crystals. Conveniently the particles will be of a magnetic metal or alloy, e.g. of pure iron, but more preferably they will be of a magnetic iron oxide, e.g. magnetite or a ferrite such as cobalt, nickel or manganese ferrites.

For use as MD agents or tracers particular mention may also be made of the paramagnetic metal complexes, especially chelate complexes, which have been proposed for use as MRI or X-ray contrast agents.

For paramagnetic metals to be administered at effective but non-toxic doses, they will generally be administered in the form of ionic or more preferably, especially at higher dosage levels, non-ionic complexes, especially chelate complexes optionally bound to larger carrier or targeting molecules which may be selected to achieve a particular biodistribution of the MD agent—e.g. to produce a blood pooling or tissue- or organ-targeting agent—or to reduce the osmolality of the MD medium by increasing the number of paramagnetic centres per MD agent molecule (or molecular ion).

A wide range of suitable chelants, polychelants, and macromolecule-bound chelants for paramagnetic metal ions has been proposed in the patent literature over the last decade and in this respect particular regard may be had to U.S. Pat. No. 4,687,659 (Quay), U.S. Pat. No. 4,647,447 (Gries), U.S. Pat. No. 4,639,365 (Sherry), EP-A-186947 (Nycomed), EP-A-299795 (Nycomed), WO-A-89/06979 (Nycomed), EP-A-331616 (Schering), EP-A-292689 (Squibb), EP-A-232751 (Squibb), EP-A-230893 (Bracco), EP-A-255471 (Schering), EP-A-277088 (Schering), EP-A-287465 (Guerbet), WO-A-85/05554 (Amersham) and the documents referred to therein, the disclosures of all of which are incorporated herein by reference.

Particularly suitable chelants for the formation of paramagnetic metal chelate MD agents for use in the method and process of the present invention include the following:

N,N,N',N'',N''-diethylenetriaminepentaacetic acid (DTPA), 6-carboxymethyl-3,9-bis(methylcarbamoylmethyl)-3,6,9-triazaundecanedioic acid (DTPA-BMA), 6-carboxymethyl-3,9-bis(morpholinocarbonylmethyl)-3,6,9-triazaundecanedioic acid (DTPA-BMO), 1,4,7,10-tetraazacyclododecane-N,N',N'',N'''-tetraacetic acid (DOTA), 1,4,7,10-tetraazacyclododecane-N,N',N''-triacetic acid (DO3A), 1-(2-hydroxypropyl)-1,4,7,10-tetraaza-N,N',N''-triacetic acid (HP-DO3A), 1-oxa-4,7,10- triazacyclododecane-N,N',N''-triacetic acid (DOXA), polylysine-bound DTPA and DTPA derivatives and DO3A and DO3A derivatives (e.g. DTPA-polylysine and DO3A-polylysine), dextran-bound DTPA and DTPA derivatives (DTPA-dextran) especially soluble materials which, having a total molecular weight $\geq 40$ KD, preferably in the range 60–100 KD, are effective as blood pooling agents.

Particularly suitable paramagnetic metal ions for chelation by such chelates are ions of metals of atomic numbers 21 to 29, 42, 44 and 57 to 71, especially 57 to 71, more especially Cr, V, Mn, Fe, Co, Pr, Nd, Eu, Gd, Tb, Dy, Ho, Er, Tm, Yb and Lu, in particular Cr(III), Cr(II), V(II), Mn(III), Mn(II), Fe(III), Fe(II) and Co(II), more especially Gd(III), Tb(III), Dy(III), Ho- (III), Er(III), Tm(III) and Yb(III), more particularly Dy(III), Ho(III) and Er(III).

In order to perform the methods of the invention with as high as possible a safety factor (the ratio between the dose of the MD agent and its $LD_{50}$), it is particularly preferred to use non-ionic or low osmolality chelates, i.e. chelates which carry no overall ionic charge, such as DyDTPA-BMA for example, or in which the complex has an overall ionic charge to paramagnetic metal centre ratio of 1.5 or less.

Furthermore, where it is desired that the MD agent should remain wholly or essentially within a body duct, e.g. the blood vessels, during passage through the body region of interest, the MD agent will preferably be particulate, hydrophilic or blood-pooling.

Examples of suitable blood-pooling agents include the inert soluble macromolecule-bound chelates of the type described by Nycomed in EP-A-186947 and WO-A-89/06979. Binding the chelant to a macromolecule, e.g. a polysaccharide such as dextran or derivatives thereof, to produce a soluble macromolecular chelant having a molecular weight above the kidney threshold, about 40 KD, ensures relatively long term retention of the contrast agent within the cardiovascular system.

Examples of suitable hydrophilic MD agents include linear, branched or macrocyclic polyaminopolycarboxylic acid chelates of paramagnetic metal ions, and also especially include chelates of chelants in which one or more carboxylic acid groupings are replaced by other groups such as amides, esters or hydroxamates, as well as such chelants in which the chelant backbone is substituted by hydrophilic groupings such as for example hydroxyalkyl or alkoxyalkyl groups. Chelants of these types are disclosed for example in U.S. Pat. No. 4,687,658 (Quay), U.S. Pat. No. 4,687,659 (Quay), EP-A-299795 (Nycomed) and EP-A-130934 (Schering).

Particular mention however must be made of the Gd(III), Dy(III), Ho(III) and Er(III) chelates of DTPA-BMA, DTPA-BMO, HP-D03A and DO3A.

Physiologically tolerable paramagnetic porphyrin complexes, especially complexes of Mn(III) and less preferably of Gd(III) or Dy(III), may also be used according to the invention with particular effect, e.g. in tumour localization. Such porphyrin complexes are described, for example, by Lyon et al. in Magnetic Resonance in Medicine 4:24–33 (1987), by Chen et al. in FEBS 1274 168:70 (1984) and in U.S. Pat. No. 4,783,529 (Lavelie). Particular mention may be made of hematoporphyrin, preferably complexed to Mn(III) but which may also be used with cobalt-58, Zinc-65 and palladium-109 as described by Bohdiewicz et al. Invest. Radiology 25:765-770 (1990). Porphyrins such as tetrakis(4-sulfonatophenyl)porphyrin (TPPS) and tetrakis(N-methyl-4-pyridyl)porphyrin (TMPyP) are already known as MRI contrast agents and are described in the literature (see for example Helpern et al. in Magnetic Resonance in Medicine 5:302-305 (1987), Patronas et al. in Cancer Treatment Reports 70 No. 3 p391 (1986), Fiel et al. in Magnetic Resonance Imaging 5:149-156 (1987) and Chen et al. supra). To accommodate a larger metal ion (e.g. Gd (III)) a so-called "expanded porphyrin" (texaphyrin) as described in WO-A-90/10633 (Univeristy of Texas), J. Am. Chen. Soc. 110:5586–5588 (1988) (Sessler et al.) and Inorganic Chemistry 28:3390–3393 (1989) (Sessler et al.) may be used according to the invention.

Moreover, magnifier paramagnetic complexes, optionally bound to targetting biomolecules or macromolecules such as those described in WO-A-90/12050 may also be used to particular effect.

The dosages of the MD agent used according to the method of the present invention will vary according to the precise nature of the MD agent used, of the magnetometer being used and of the tissue or organ of interest. Preferably however the dosage should be kept as low as possible while still achieving a detectable variation in magnetic susceptibility.

In general, the MD agents used according to the invention should be administered in a quantity sufficient to produce a concentration, expressed in terms of susceptibility of at least $10^{-9}$ emu/g, preferably at least $5 \times 10^{-9}$ emu/g, especially at least $10^{-8}$ emu/g.

Thus viewed from a further aspect the invention provides a magnetic susceptibility MD medium in aqueous form containing a physiologically tolerable paramagnetic or superparamagnetic substance together with at least one pharmaceutical carrier or excipient, the magnetic susceptibility of said medium (at STP) being in the range $10^{-12}$ to $10^{-6}$, preferably $10^{-11}$ to $2 \times 10^{-7}$, especially preferably $10^{-10}$ to $5 \times 10^{-8}$, in particular $10^{-9}$ to $10^{-8}$, emu/g.

Alternatively expressed, for most paramagnetic and superparamgnetic materials the novel MD media will conveniently contain the magnetic metal at a concentration of at least $10^{-14}M$, generally at least $10^{-10}M$, preferably at least $10^{-8}M$, in particular at least 0.05 mM, especially at least 0.2 mM, more preferably at least 0.3 mM, most preferably at least 1.0 mM, e.g. 0.0002 to 2M, more especially 0.0003 to 1.5M.

The MD media of the invention may contain particularly low concentrations of the contrast agent where it is a highly specifically targeted material. Thus for an agent specific for small tumours minimum dosages of the order of $10^{-14}M/Kg$ may be adequate, for liver specific agents minimum dosages may be of the order of $10^{-11}M/Kg$ and for agents which distribute broadly within the body minimum dosages of $10^{-10}M/kg$ may be appropriate. These will generally be administered in volumes of 0.1 ml to 1000 ml. The upper limit for MD agent dosages will be generally comparable to that for MRI contrast agents and may be dictated by toxicity constraints.

For most MD agents the appropriate dosage will generally lie in the range 0.02 $\mu$mol to 3 mmol paramagnetic metal/kg bodyweight, especially 1 $\mu$mol to 1.5 mmol/kg, particularly 0.01 to 0.5, and more especially 0.1 to 0.4 mmol/kg.

Where less sensitive non-SQUID magnetometers are used according to the invention, the MD agent concentrations required will of course be higher than are needed using SQUID magnetometers.

It is well within the skill of the average practitioner in this field to determine the optimum dosage for any particular MD agent by simple experiment, either in vivo or in vitro.

Where the MD agent is ionic, such as is the case with DyDTPA, it will conveniently be used in the form of a salt with a physiologically acceptable counterion, for example an ammonium, substituted ammonium, alkali metal or alkaline earth metal cation or an anion deriving from an inorganic or organic acid. In this regard, meglumine salts are particularly preferred.

MD agents may be formulated with conventional pharmaceutical or veterinary aids, for example, stabilizers, antioxidants, osmolality adjusting agents, buffers, pH adjusting agents, etc., and may be in a form suitable for enteral or parenteral administration, e.g. oral, rectal, intravascular etc. Particularly preferably the MD agents will be in forms suitable for ingestion, injection or infusion directly or after dispersion in or dilution with a physiologically acceptable carrier medium, e.g. water for injections. Thus the contrast agents may be formulated in conventional administration forms such as powders, solutions, suspensions, dispersions etc., however solutions, suspensions and dispersions in physiologically acceptable carrier media will generally be preferred.

The MD agents may therefore be formulated for administration using physiologically acceptable carriers or excipients in a manner fully within the skill of the art. For example, the MD agents optionally with the addition of pharmaceutically acceptable excipients, may be suspended or dissolved in an aqueous medium, with the resulting solution or suspension then being sterilized. Suitable additives include, for example, physiologically biocompatible buffers chelating agents (as for example DTPA or DTPA-bisamide (e.g. 6-carboxymethyl-3,9-bis(methylcarbamoyl methyl)-3,6,9-triazaundecanedioic acid)) or calcium chelate complexes (as for example salt forms of the calcium DTPA complex or the calcium DTPA-bisamide complex, such as NaCaDTPA-bisamide) or, optionally, additions (e.g. 1 to 50 mole percent) of calcium or sodium salts (for example, calcium chlorie, calcium ascorbate, calcium gluconate or calcium lactate and the like).

Parenterally administerable forms, e.g., intravenous solutions, should of course be sterile and free from physiologically unacceptable agents, and should have low osmolality to minimize irritation or other adverse effects upon administration and thus the MD medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington American Pharmaceutical Association (1975). The solutions can contain preservatives, antimicrobial agents, buffers and antioxidants conventionally used for parenteral solutions, excipients and other additives which are compatible with the MD agents and which will not interfere with the manufacture, storage or use of the products.

It will be realized of course that since the MRI contrast media can be used as MD media it will be particularly convenient to investigate the subject using MRI to supplement or confirm diagnostic information derived from the magnetometer investigations. Moreover, images from MRI on other conventional imaging modalities may be used to provide a "native" image onto which the magnetometric information or image may be superimposed—this is of particular value where the biodistribution of the magnetometric contrast agent is very limited.

The invention will now be illustrated further with reference to the following non-limiting Examples.

EXAMPLE 1

Intravenous superparamagnetic MD agent for liver, spleen and perfusion studies (Dextran-coated superparamagnetic particles)

Dextran-coated superparamagnetic particles are prepared from $FeCl_2$, $FeCl_3$ and dextran according to Example 7.1 in WO-A-88/00060 (Advanced Magnetics). Average particle size: 140 nm An injectable dispersion is prepared which contains: Dextran-coated superparamagnetic particles 20 mg Saline solution (0.9% sodium chloride) ad 10 ml.

The superparamagnetic particles are dispersed in saline solution and filled into 10 ml vials under aseptic conditions. The suspension is sonicated before administration to ensure complete dispersion of the particles.

EXAMPLE 2

Intravenous superparamagnetic MD agent for tumour studies (Monoclonal antibody-coated magnetite particles)

Monoclonal antibody-coated superparamagnetic particles are prepared according to the method of S. Cerdan et al., Magnetic Resonance in Medicine 12:151-163 (1989).

The antibody is 33B31 (an antibody to IL-2 available from Immunotech), PP1 (an antibody to sarcoma available from Fodstad, Norwegian Radium Hospital, Oslo), or S4H9 (an antibody to the D2 fragment of fibrinogen available from Nycomed AS).

A dispersion of the particles is filled into 20 ml vials and freeze dried. Each vial contains 48 mg Fe.

The product is dispersed in 10 ml saline before administration.

EXAMPLE 3

Intravenous paramagnetic MD agent for tumour studies (Monoclonal antibody labelled with stable free radicals)

2,2,5,5-tetramethyl-3-aminopyrrolidone-1-oxide radical is coupled to monoclonal antibody according to the methods described in U.S. Pat. No. 3,453,288.

The antibody is as in Example 2.

A solution of the labelled antibody is filled into 10 ml vials and freeze dried. Each vial contains 0.5 mmol nitroxide radicals.

The product is dissolved in 5 ml saline before use.

EXAMPLE 4

Intravenous paramagnetic MD agent for perfusion studies (Dextran 70-beta-alanine-DOTA-Dy)

Dextran 70-beta-alanine-DOTA-Dy is prepared according to Example 6 in EP-A-326226 (Nycomed).

An injectable solution is prepared which contains:

| | |
|---|---|
| Dextran 70-beta-alanine-DOTA-Dy | 2320 mg |
| Saline solution | ad 10 ml. |

Dextran 70-beta-alanine-DOTA-Dy is dissolved in saline solution and filled into 10 ml vials under aseptic conditions. The solution contains 0.14 mmol Dy/ml.

EXAMPLE 5

Intravenous paramagnetic MD agent (Dy(III)-DO3A)

Dysprosium(III)(1,4,7-triscarboxymethyl-1,4,7,10-tetra azacyclododecane (Dy(III)-DO3A) is prepared according to Example 10 in EP-A-232751.

An injectable solution is prepared which contains:

| | |
|---|---|
| Dy(III)-DO3A | 2 mmol |
| Water for injections | ad 20 ml |

Dy(III)-DO3A is dissolved in water for injection, filled into 20 ml vials and sterilized by heating.

EXAMPLE 6

Intravenous paramagnetic MD agent (Gd(III)-DTPA)

Gadolinium(III)-diethylenetriamine-N,N,N',N'',N''-pentaacetic acid di-N-methylglucamine salt (Gd(III)-DTPA) was prepared according to Example 5 in U.S. Pat. No. 4,647,447 (Schering).

An injectable solution is prepared which contains:

| Gd(III)-DTPA dimeglumine | 10 mmol |
|---|---|
| CaNa₃-DTPA | 0.1 mmol |
| Water for injections | ad 20 ml |

Gd(III)-DTPA dimeglumine and CaNa₃DTPA are dissolved in water for injections, filled into 20 ml vials and sterilized by heating.

EXAMPLE 7

Intravenous MD agent (Liposome formulation of Dy(III)-DTPA)

Dysprosium(III)-diethylenetriamine-N,N,N',N'',N''-pent aacetic acid di-N-methylglucamine salt (Dy(III)-DTPA dimeglumine) is prepared according to Example 5 in U.S. Pat. No. 4,647,447 (Schering).

Dy(III)-DTPA dimeglumine is encapsulated into small unilamellar vesicles according to the method described in EP-A-160552 (Vestar).

The purified liposome dispersion is filled into 50 ml vials and freeze dried. Each vial contains 0.5 mmol dysprosium.

The product is suspended in 20 ml saline before administration.

EXAMPLE 8

Intravenous paramagnetic MD agent for tumour studies (Monoclonal antibody labelled with dysprosium)

Diethylenetriamine-N,N,N', N'', N'''-pentaacetic acid is coupled to monoclonal antibodies according to the method described by D J Hnatowich et al. in Science 220:613–615.

The antibody is as in Example 2.

1.0 mole equivalent dysprosium chloride is added during agitation, the pH-value is adjusted to 5.2 and the solution is agitated for 1 hour.

The solution is dialyzed against saline for 2 days then dialyzed against distilled water. The aqueous solution is filled into 5 ml vials and lyophilized. Each vial contains 1 mmol dysprosium.

The product is dissolved in 5 ml or for lower concentrations 500 ml saline before use, in the latter case only 5 ml being injected.

EXAMPLE 9

Oral superparamagnetic MD agent for abdominal studies

Particles of a sulphonated styrene-divinylbenzene copolymer matrix 3 micrometers in size and themselves carrying superparamagnetic particles to a total iron content of 19.4% by weight are prepared by the methods of WO-A-83/03920 (SINTEF)

A suspension for oral administration is prepared which contains:

| Superparamagnetic particles | 0.1 g |
|---|---|
| Hydroxyethyl cellulose | 8.0 g |
| Methyl parahydroxybenzoate | 0.7 g |
| Propyl parahydroxybenzoate | 0.15 g |
| Ethanol | 10.0 g |
| Saccharin sodium | 1.0 g |
| Anis essence | 0.2 g |
| Water | ad 800 g |

Hydroxyethyl cellulose is dispersed in water with stirring for 2 hours. Saccharin sodium and a solution of anis essence, methyl and propyl prahydroxybenzoate in ethanol are slowly added. The superparamagnetic particles are dispersed in the solution under vigorous stirring.

The suspension is filled into a 800 ml bottle. The suspension contains 19.4 mg iron.

EXAMPLE 10–11

Multi-channel SQUID analysis of 0.5% agar gels containing MD agents.

SQUID Instrument: Krenikon (SIMENS AG)

All samples were moved with the same frequency (appr. 4 Hz) during the experiments.

SQUID signals (16 channels) without sample is shown in FIG. 1.

EXAMPLE 10

Figure 2:
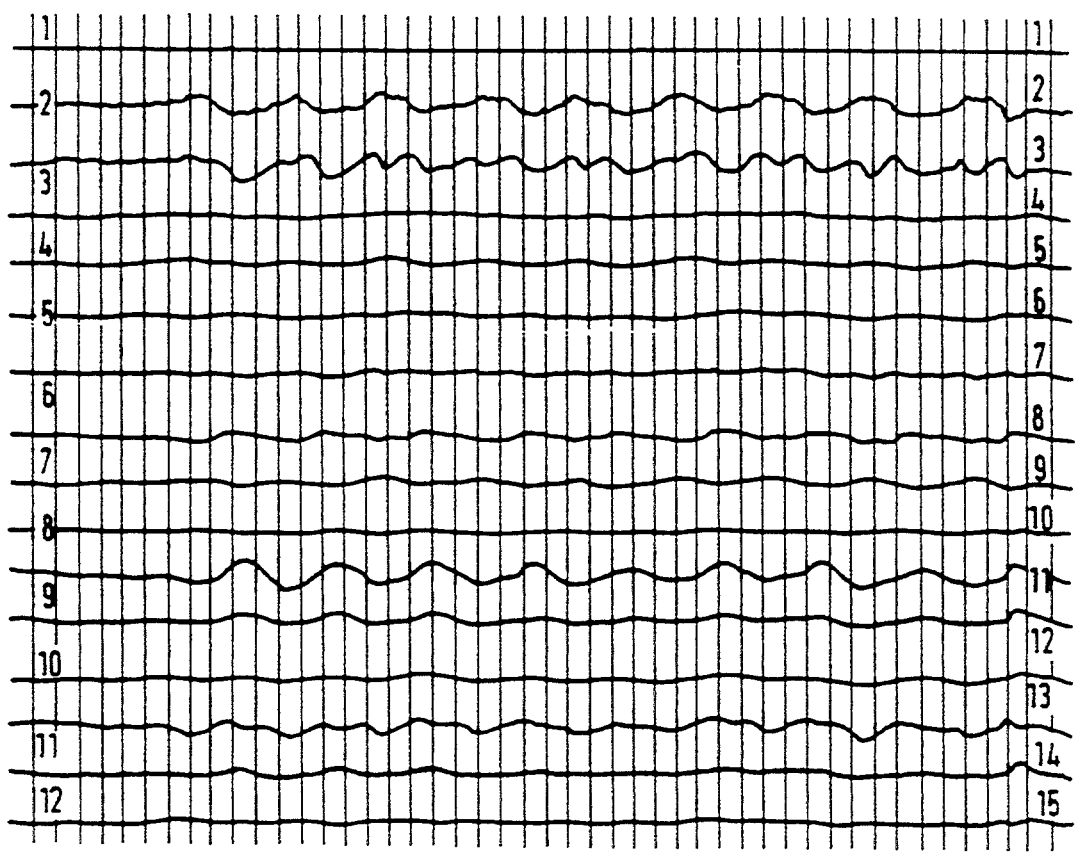
FIG. 2 represents a multichannel SQUID analysis using starch microspheres according to Schroder et al.

MD agent: Superparamagnetic starch microspheres prepared according to (Schroder and Salford)
Concentration: 0.1 mmol/kg
Distance from detector: 1 cm
Results shown in FIG. 2.

EXAMPLE 11

Figure 3:
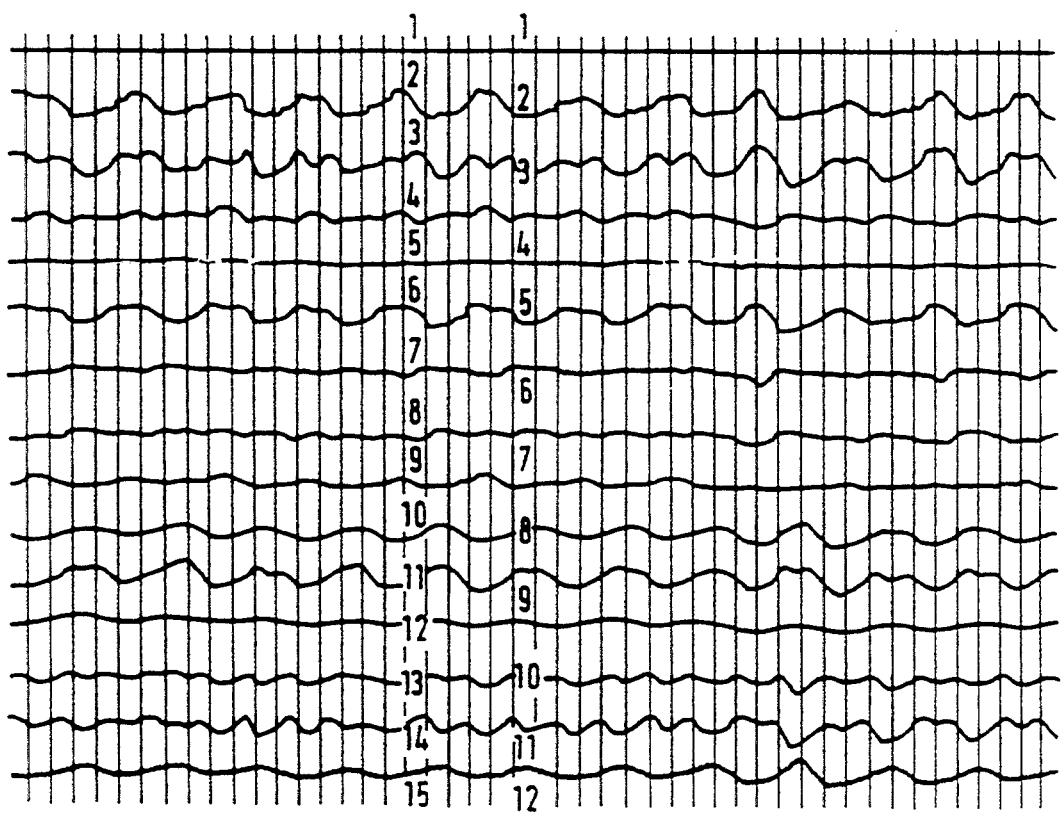
FIG. 3 represents a multichannel SQUID analysis using Gd-DTPA BMA prepared according to Quay.

MD agent: GdDTPA-BMA prepared according to U.S. Pat. No. 4,687,658 (Quay)
Concentration: 0.1 mmol/kg
Distance from detector: 1 cm
Results shown in FIG. 3.

EXAMPLE 12–13

Multi-channel SQUID analysis of the same samples as described in Example 10–11 after magnetization of the samples with a small, strong (about 0.3 T) permanent magnet showed enhanced magnetometric effect compared to the non-magetized samples.

(No corrections have been made for potential magnetization of the empty plastic test tubes).

EXAMPLES 14–15

SQUID analysises of the samples in Examples 19–26 are performed on an instrument detecting magnetic fields. Enhanced efficiency is observed.

(The instrument used in Examples 10–13 detects magnetic field gradients and not the absolute magnetic fields).

EXAMPLES 16 to 22

Low concentration intravenous MD media

The MD media of Examples 1 to 7 are diluted, 1 part by volume with 99 parts by volume of water for injections to produce more dilute contrast media suitable for use with sensitive SQUID based magnetometers.

Still lower concentrations, e.g. at the $10^{-10} - 10^{-6}$M level, can be produced by further dilution.

We claim:

1. A method of generating a magnetometric image of the human or non-human animal body comprising administering to said body a physiologically tolerable superparamagnetic material and generating a magnetometric signal of at least part of said body into which said material distributes.

2. A method as claimed in claim 1, wherein said signal is a magnetometric image of at least part of said body into which said material distributes.

3. A method as claimed in claim 2, wherein said image generated is a two or three dimensional structural image.

4. A method as claimed in claim 1, wherein said signal is generated using a superconducting quantum interference device (SQUID) magnetometer.

5. A method as claimed in claim 4, wherein said signal is generated using a multichannel SQUID system.

6. The method as claimed in claim 1, wherein a superparamagnetic material is used as a magnetometric diagnostic (MD) agent with no pre-magnetization thereof and no magnetic field or with a static magnetic field being imposed during signal generation.

7. A process for detecting variations in magnetic susceptibility within a human or non-human animal body, comprising administering to said body a physiologically tolerable superparamagnetic material, and with a magnetometer continuously or repeatedly monitoring the magnetic susceptibility of at least a part of said body into which said material distributes.

8. A process as claimed in claim 7 comprising generating a magnetometric image.

9. A process as claimed in claim 7, wherein said magnetometer is a superconducting quantum interference device (SQUID) magnetometer.

10. A process as claimed in claim 9, wherein said magnetometer is a multichannel SQUID system.

11. The process as claimed in claim 7, wherein a superparamagnetic material is used as a magnetometric diagnostic (MD) agent with no pre-magnetization thereof and no magnetic field or with a static magnetic field being imposed during signal generation.

* * * * *